(12) United States Patent
Yehezkely et al.

(10) Patent No.: US 10,063,211 B2
(45) Date of Patent: Aug. 28, 2018

(54) COMPACT BYPASS AND DECOUPLING STRUCTURE FOR MILLIMETER-WAVE CIRCUITS

(71) Applicant: QUALCOMM Incorporated, San Diego, CA (US)

(72) Inventors: Alon Yehezkely, Haifa (IL); Sagi Kupferman, Givataim (IL)

(73) Assignee: QUALCOMM Incorporated, San Diego, CA (US)

(*) Notice: Subject to any disclaimer, the term of this patent is extended or adjusted under 35 U.S.C. 154(b) by 0 days.

(21) Appl. No.: 15/422,434

(22) Filed: Feb. 1, 2017

(65) Prior Publication Data

US 2017/0222613 A1 Aug. 3, 2017

Related U.S. Application Data

(60) Provisional application No. 62/290,890, filed on Feb. 3, 2016.

(51) Int. Cl.
*H04B 1/38* (2015.01)
*H03H 7/01* (2006.01)
(Continued)

(52) U.S. Cl.
CPC ........... *H03H 7/0115* (2013.01); *H01L 23/50* (2013.01); *H01L 23/5223* (2013.01);
(Continued)

(58) Field of Classification Search
USPC .............. 455/73.1, 550.1, 63.1, 67.11, 127.1
See application file for complete search history.

(56) References Cited

U.S. PATENT DOCUMENTS 8,653,907 B2 2/2014 Mooney et al.
9,496,948 B2 11/2016 Yehezkely et al.
(Continued)

FOREIGN PATENT DOCUMENTS

JP 2001102882 A 4/2001
WO 2011017368 A1 2/2011

OTHER PUBLICATIONS

Wang Y., et al., "Widely Tunable Inductors Utilizing Transmission-line with Variable Distributed Load Capacitor for Millimeter-wave Applications," PIERS Proceedings, Aug. 2014, pp. 378-382.
(Continued)

*Primary Examiner* — Fayyaz Alam
(74) *Attorney, Agent, or Firm* — Muncy, Geissler, Olds & Lowe, P.C.

(57) ABSTRACT

The disclosure generally relates to a compact bypass and decoupling structure that can be used in a millimeter-wave radio frequency integrated circuit (RFIC). For example, according to various aspects, an RFIC incorporating the compact bypass and decoupling structure may comprise a grounded substrate, a mid-metal ground plane, a bypass capacitor disposed between the grounded substrate and the mid-metal ground plane, and a decoupling inductor disposed over the mid-metal ground plane. The bypass capacitor may close a current loop in the RFIC and the decoupling inductor may provide damping in a supply network associated with the RFIC. Furthermore, the decoupling conductor may have a self-resonance substantially close to an operating band associated with the RFIC to increase series isolation, introduce substrate losses that facilitate the damping in the supply network, and prevent high-Q resonances.

22 Claims, 15 Drawing Sheets

(51) Int. Cl.
  *H04B 1/40*    (2015.01)
  *H03F 3/195*   (2006.01)
  *H03F 1/02*    (2006.01)
  *H01L 23/50*   (2006.01)
  *H01L 23/522*  (2006.01)
  *H03F 1/56*    (2006.01)
  *H03F 3/193*   (2006.01)

(52) U.S. Cl.
  CPC ....... *H01L 23/5227* (2013.01); *H03F 1/0222* (2013.01); *H03F 1/565* (2013.01); *H03F 3/193* (2013.01); *H03F 3/195* (2013.01); *H04B 1/40* (2013.01); *H03F 2200/294* (2013.01); *H03F 2200/408* (2013.01); *H03F 2200/451* (2013.01)

(56) References Cited

U.S. PATENT DOCUMENTS

| | | |
|---|---|---|
| 2002/0020894 A1 | 2/2002 | Nishijima |
| 2004/0000951 A1* | 1/2004 | Stengel ................. H03F 3/605 330/286 |
| 2004/0081811 A1 | 4/2004 | Casper et al. |
| 2005/0208921 A1 | 9/2005 | Roufoogaran |
| 2006/0141978 A1 | 6/2006 | Liu |
| 2008/0122560 A1 | 5/2008 | Liu |
| 2008/0180178 A1* | 7/2008 | Gao ........................ H03F 1/565 330/302 |
| 2011/0070848 A1* | 3/2011 | Ramachandra Reddy .................. H03F 1/0227 455/127.2 |
| 2012/0037969 A1 | 2/2012 | Sanders et al. |
| 2012/0086114 A1 | 4/2012 | Zhao et al. |
| 2013/0328640 A1 | 12/2013 | Tsutsumi |
| 2014/0320205 A1 | 10/2014 | Lyalin et al. |
| 2015/0194736 A1 | 7/2015 | Diukman et al. |
| 2015/0381121 A1 | 12/2015 | Jones et al. |
| 2016/0241295 A1* | 8/2016 | Lyalin .................. H03F 1/0288 |

OTHER PUBLICATIONS

International Search Report and Written Opinion—PCT/US2017/016142—ISA/EPO—dated Apr. 21, 2017.

* cited by examiner

COMPACT BYPASS AND DECOUPLING STRUCTURE FOR MILLIMETER-WAVE CIRCUITS

CROSS-REFERENCE TO RELATED APPLICATIONS

The present application claims the benefit of U.S. Provisional Patent Application No. 62/290,890 entitled "COMPACT BYPASS AND DECOUPLING STRUCTURE FOR MILLIMETER-WAVE CIRCUITS," filed Feb. 3, 2016, assigned to the assignee hereof, and expressly incorporated herein by reference in its entirety.

TECHNICAL FIELD

The various aspects and embodiments described herein generally relate to radio frequency integrated circuits, and more particularly, to a compact bypass and decoupling structure designed to be used in a millimeter-wave circuit.

BACKGROUND

Growth in mobile traffic demands has been driving demand to have wireless devices with capabilities to communicate at higher frequencies and with higher bandwidth. Frequency bands that wireless devices use to communicate have risen from megahertz (MHz) to the low gigahertz (GHz). The next step in this progression involves frequencies in the millimeter-wave (mmWave) band from 30 GHz to 300 GHz (e.g., as specified in the IEEE 802.11ad (WiGig) standard and proposed to be used in 5G mobile networks). The millimeter-wave frequency band offers the potential to provide multi-gigabit services, including high-definition television (HDTV), ultra-high definition video (UHDV), wireless docking stations, wireless Gigabit Ethernet, among others. However, because radio waves in the millimeter-wave frequency band have very short wavelengths, from one to ten millimeters, millimeter-wave communications are subject to atmospheric absorption that limits propagation to a few kilometers or less (e.g., line-of-sight), sensitivity to blockage, and other challenges. Furthermore, radio frequency integrated circuits designed to be used in millimeter-wave communications are subject to additional challenges. For example, radio frequency integrated circuits face problems that relate to phase noise and IQ imbalance that can occur due to mismatches between parallel sections in a receiver chain that deal with in-phase (I) and quadrature (Q) signal paths. Furthermore, the transmit power and bandwidth needed to communicate at high carrier frequencies and with wide bandwidth results in power amplifiers experiencing significant nonlinear distortion. Accordingly, there are significant needs to have radio frequency integrated circuits with designs that can be used in millimeter-wave communications and/or other future wireless technologies.

SUMMARY

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

According to various aspects, a radio frequency integrated circuit (RFIC) may comprise a compact bypass and decoupling structure suitable to use in a millimeter-wave circuit (e.g., an 802.11ad WiGig transceiver configured to transmit and receive millimeter-wave wireless signals in a 60 GHz frequency band, a cellular transceiver configured to transmit and receive millimeter-wave wireless signals in a 28 GHz and/or a 39 GHz frequency band, etc.). For example, according to various embodiments, the RFIC may comprise a grounded connection, a mid-metal ground plane, a bypass capacitor disposed between the grounded connection and the mid-metal ground plane, and a supply decoupling inductor disposed over the bypass capacitor, wherein the bypass capacitor may be arranged to close a current loop in the RFIC and the decoupling inductor may be arranged to provide damping and isolation in a supply network associated with the RFIC. Furthermore, the decoupling conductor may have a self-resonance substantially close to an operating band associated with the RFIC to increase series isolation, introduce substrate losses that facilitate the damping in the supply network, and prevent high-Q resonances without the need to introduce resistance on a supply line. Accordingly, the RFIC design described herein may improve instability concerns and/or risks in the millimeter-wave circuit (e.g., in close proximity compact amplifiers that are sensitive to instability due to the supply network coupling signals from gain stage outputs to inputs). Moreover, the RFIC design described herein may provide simpler matching between blocks and reduce the area associated with gain elements (e.g., in a power amplifier, a low noise amplifier, a variable gain amplifier, etc.).

Other objects and advantages associated with the aspects and embodiments disclosed herein will be apparent to those skilled in the art based on the accompanying drawings and detailed description.

BRIEF DESCRIPTION OF THE DRAWINGS

A more complete appreciation of the various aspects and embodiments described herein and many attendant advantages thereof will be readily obtained as the same becomes better understood by reference to the following detailed description when considered in connection with the accompanying drawings which are presented solely for illustration and not limitation, and in which.

DETAILED DESCRIPTION

Various aspects and embodiments are disclosed in the following description and related drawings to show specific examples relating to exemplary aspects and embodiments. Alternate aspects and embodiments will be apparent to those skilled in the pertinent art upon reading this disclosure, and may be constructed and practiced without departing from the scope or spirit of the disclosure. Additionally, well-known elements will not be described in detail or may be omitted so as to not obscure the relevant details of the aspects and embodiments disclosed herein.

The word "exemplary" is used herein to mean "serving as an example, instance, or illustration." Any embodiment described herein as "exemplary" is not necessarily to be construed as preferred or advantageous over other embodiments. Likewise, the term "embodiments" does not require that all embodiments include the discussed feature, advantage, or mode of operation.

The terminology used herein describes particular embodiments only and should not be construed to limit any embodiments disclosed herein. As used herein, the singular forms "a," "an," and "the" are intended to include the plural forms as well, unless the context clearly indicates otherwise. Those skilled in the art will further understand that the terms "comprises," "comprising," "includes," and/or "including," as used herein, specify the presence of stated features, integers, steps, operations, elements, and/or components, but do not preclude the presence or addition of one or more other features, integers, steps, operations, elements, components, and/or groups thereof.

Further, various aspects and/or embodiments may be described in terms of sequences of actions to be performed by, for example, elements of a computing device. Those skilled in the art will recognize that various actions described herein can be performed by specific circuits (e.g., an application specific integrated circuit (ASIC)), by program instructions being executed by one or more processors, or by a combination of both. Additionally, these sequences of actions described herein can be considered to be embodied entirely within any form of non-transitory computer-readable medium having stored thereon a corresponding set of computer instructions that upon execution would cause an associated processor to perform the functionality described herein. Thus, the various aspects described herein may be embodied in a number of different forms, all of which have been contemplated to be within the scope of the claimed subject matter. In addition, for each of the aspects described herein, the corresponding form of any such aspects may be described herein as, for example, "logic configured to" and/or other structural components configured to perform the described action.

Figure 1:
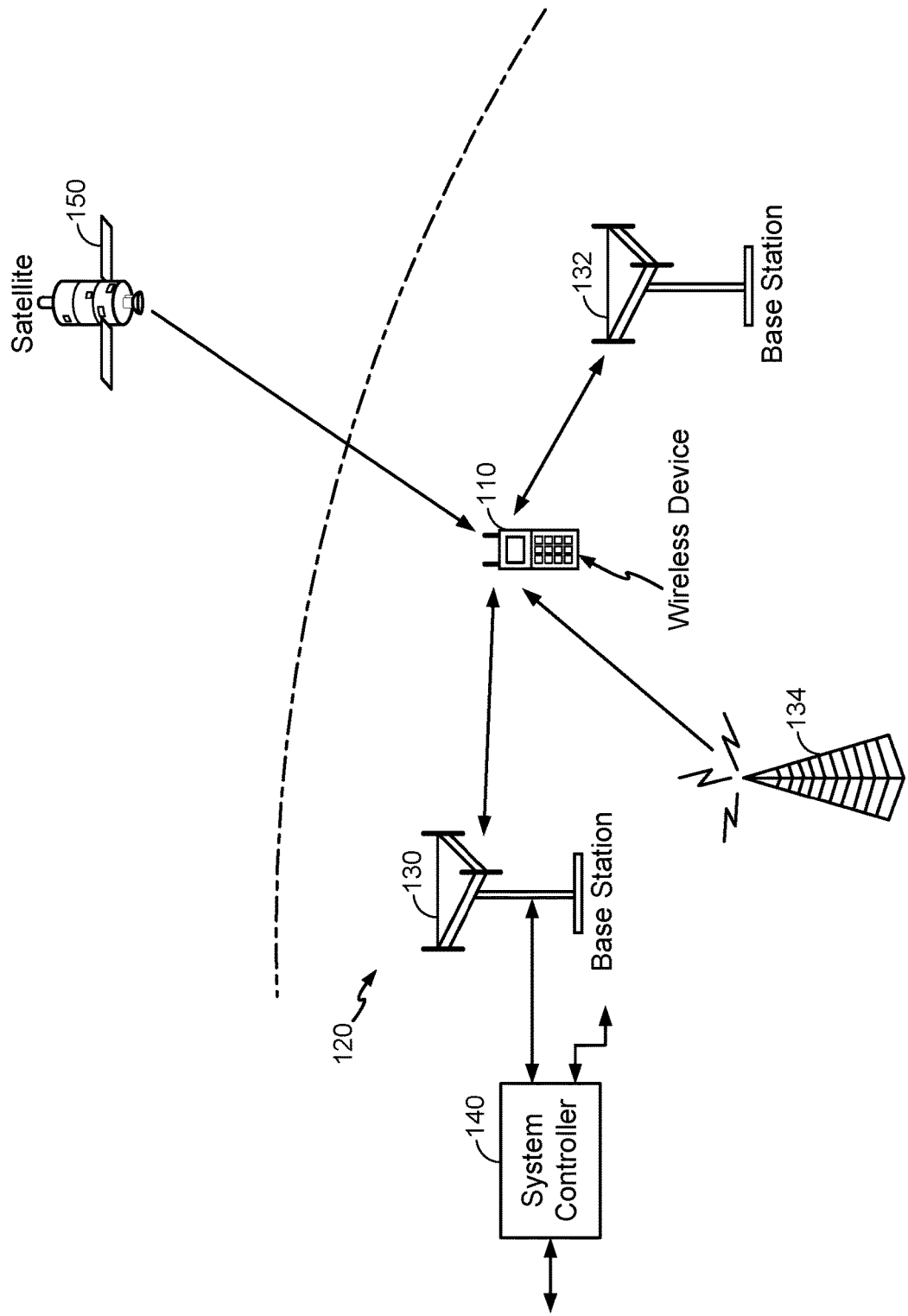
FIG. 1 illustrates an example wireless system, according to various aspects.

According to various aspects, FIG. 1 illustrates an exemplary wireless communication system 120 in which a wireless device 110 may communicate with other entities. In various embodiments, the wireless device 110 may include an antenna 112, which may be part of an antenna array. The wireless communication system 120 may be a Long Term Evolution (LTE) system, a Code Division Multiple Access (CDMA) system, a Global System for Mobile Communications (GSM) system, a wireless local area network (WLAN) system, a 60 GHz system, a millimeter-wave system, a system that operates in accordance with one or more Institute of Electrical and Electronics Engineers (IEEE) 802.11 standards or protocols, or some other wireless system. A CDMA system may implement Wideband CDMA (WCDMA), CDMA 1X, Evolution-Data Optimized (EVDO), Time Division Synchronous CDMA (TD-SCDMA), or some other version of CDMA. For simplicity, the wireless communication system 120 shown in FIG. 1 includes two base stations 130 and 132 and one system controller 140. However, those skilled in the art will appreciate that the wireless communication system 120 may include any suitable number of base stations and any suitable set of network entities.

In various embodiments, the wireless device 110 may also be referred to as user equipment (UE), a mobile station, a terminal, an access terminal, a subscriber unit, a station, etc. The wireless device 110 may be a cellular phone, a smartphone, a tablet, a wireless modem, a personal digital assistant (PDA), a handheld device, a laptop computer, a smartbook, a netbook, a cordless phone, a wireless local loop (WLL) station, a Bluetooth device, etc. The wireless device 110 may communicate with various other entities within the wireless communication system 120. The wireless device 110 may also receive signals from broadcast stations (e.g., a broadcast station 134), signals from satellites in one or more global navigation satellite systems (GNSS) (e.g., a satellite 150), etc. The wireless device 110, the base stations 130, 132, the broadcast station 134, etc. may support one or more radio technologies for wireless communication such as LTE, WCDMA, CDMA 1X, EVDO, TD-SCDMA, GSM, 802.11, 60 GHz, millimeter-wave, etc. As such, according to the various aspects and embodiments described herein, the wireless device 110, the base stations 130, 132, the broadcast station 134, and/or any other suitable entities that can communicate in the millimeter-wave frequency band using one or more components that implement a radio frequency integrated circuit with a compact bypass capacitor and decoupling inductor structure design, an example of which is provided below with reference to FIG. 5.

Figure 2:
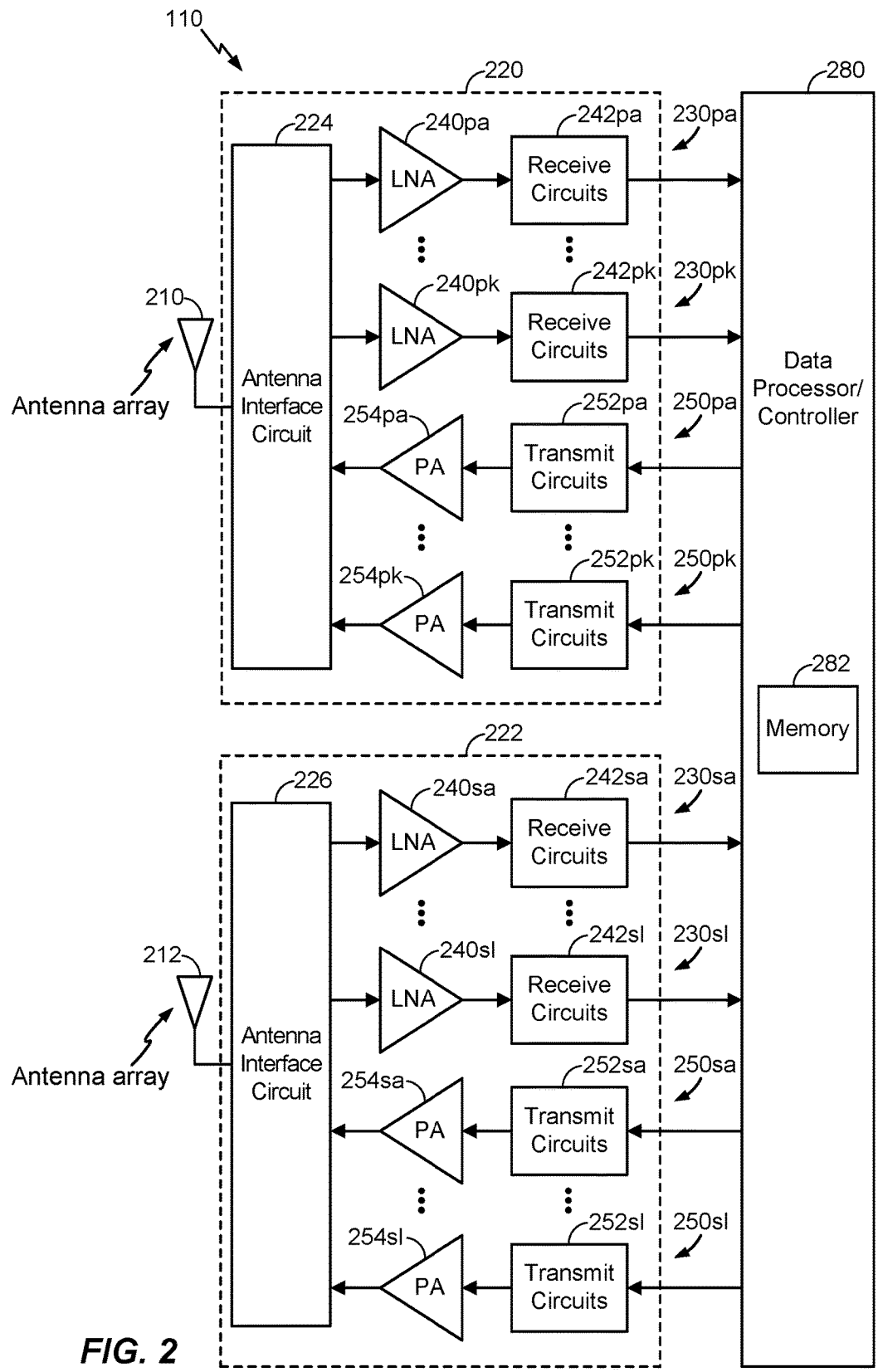
FIG. 2 illustrates an example wireless device, according to various aspects.
Figure 5:
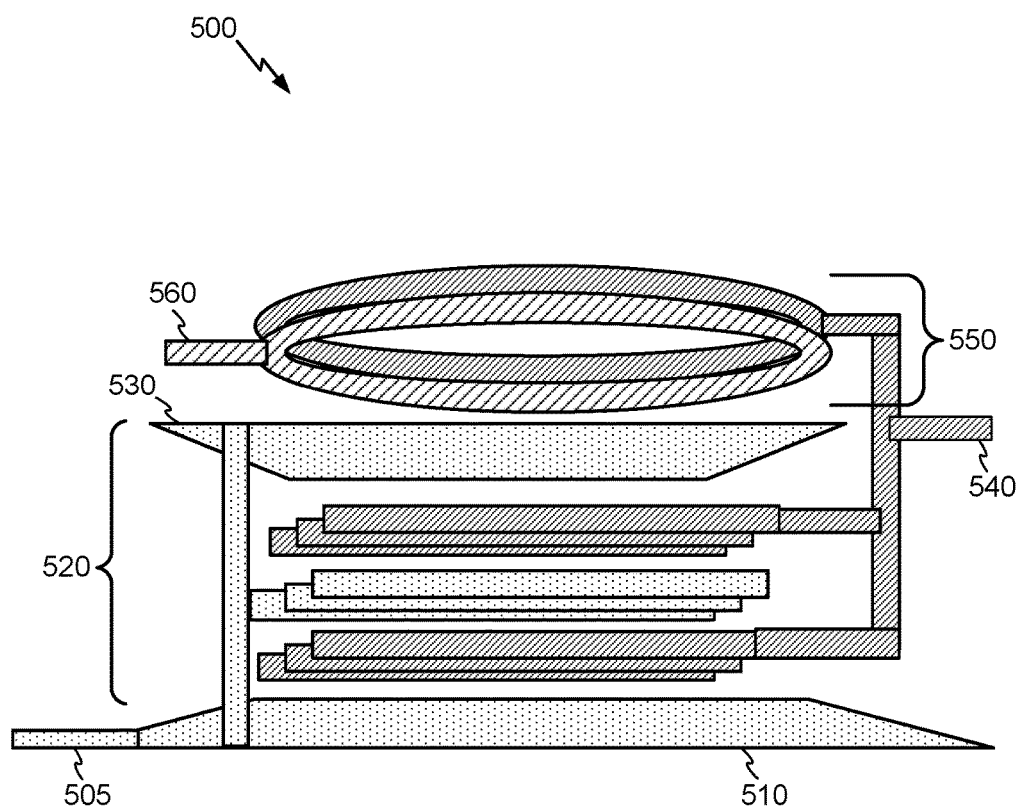
FIG. 5 illustrates an example radio frequency integrated circuit with a compact bypass capacitor and decoupling inductor structure, according to various aspects.

According to various aspects, FIG. 2 illustrates an example wireless device 110, which may correspond to the wireless device 110, the base stations 130, 132, and/or the broadcast station 134 shown in FIG. 1 and/or any other suitable wireless device that can communicate in the millimeter-wave frequency band using one or more components that implement a radio frequency integrated circuit with a compact bypass capacitor and decoupling inductor structure design, an example of which is provided below with reference to FIG. 5. In the exemplary design shown in FIG. 2, the wireless device 110 includes a transceiver 220 coupled to a primary antenna array 210, a transceiver 222 coupled to a secondary antenna array 212 (e.g., via antenna interface circuit 226), and a data processor/controller 280. For example, in various embodiments, the transceiver 220 may comprise an 802.11ad WiGig transceiver configured to transmit and receive millimeter-wave wireless signals in a 60 GHz frequency band and the transceiver 222 may comprise a cellular transceiver configured to transmit and receive millimeter-wave wireless signals in a 28 GHz and/or 39 GHz frequency band. Furthermore, in various embodiments, the transceivers 220, 222 may comprise at least one radio frequency integrated circuit having the compact bypass capacitor and decoupling inductor structure described herein. However, the transceivers 220, 222 may have other possible configurations. In various embodiments, the antenna arrays 210, 212 may be separate or part of a single larger antenna array, and the transceiver 220 may include multiple (K) receivers 230*pa* to 230*pk* and multiple (K) transmitters 250 *pa* to 250*pk* to support multiple frequency bands, multiple radio technologies, carrier aggregation, etc. The transceiver 222 may include multiple (L) receivers 230*sa* to 230*s1* and multiple (L) transmitters 250*sa* to 250s1 to support multiple frequency bands, multiple radio technologies, carrier aggregation, receive diversity, multiple-input multiple-output (MIMO) transmission from multiple transmit antennas to multiple receive antennas, etc.

In the exemplary design shown in FIG. 2, each receiver 230 may include a low noise amplifier (LNA) 240 and one or more receive circuits 242. For data reception, the primary antenna array 210 may receive signals from one or more base stations and/or other transmitter stations and provide a received RF signal, which may be routed through an antenna interface circuit 224 and presented as an input RF signal to a selected receiver. The antenna interface circuit 224 may include one or more switches, duplexers, transmit filters, receive filters, matching circuits, etc. The description below assumes that receiver 230pa is the selected receiver. Within receiver 230pa, an LNA 240pa may amplify the input RF signal and provide an output RF signal. The receive circuits 242pa may downconvert the output RF signal from RF to baseband, amplify and filter the downconverted signal, and provide an analog input signal to data processor/controller 280. The receive circuits 242pa may include mixers, filters, amplifiers, matching circuits, an oscillator, a local oscillator (LO) generator, a phase locked loop (PLL), etc. Each remaining receiver 230 in transceivers 220 and 222 may operate in a similar manner as receiver 230pa.

In the exemplary design shown in FIG. 2, each transmitter 250 may further include one or more transmit circuits 252 and a power amplifier (PA) 254. For data transmission, data processor/controller 280 may process (e.g., encode and modulate) data to be transmitted and provide an output signal to a selected transmitter. The description below assumes that transmitter 250pa is the selected transmitter. Within transmitter 250pa, transmit circuits 252pa may amplify, filter, and upconvert the output signal from baseband to RF and provide a modulated RF signal. Transmit circuits 252pa may include amplifiers, filters, mixers, matching circuits, an oscillator, an LO generator, a PLL, etc. A PA 254pa may receive and amplify the modulated RF signal and provides a transmit RF signal. The transmit RF signal may be routed through antenna interface circuit 224 and transmitted via the antenna array 210. Each remaining transmitter 250 in transceivers 220 and 222 may operate in a similar manner as transmitter 250pa.

Although the example design shown in FIG. 2 illustrates receiver 230 and transmitter 250 designs, a receiver and a transmitter may also include other circuits not shown in FIG. 2, such as filters, matching circuits, etc. For example, as mentioned above, a receiver 230, a transmitter 250, and/or a transceiver incorporating a receiver 230 and a transmitter 250 may include the radio frequency integrated circuit with the compact bypass capacitor and decoupling inductor structure shown in FIG. 5. All or a portion of the transceivers 220 and 222 may be implemented on one or more analog integrated circuits, radio frequency integrated circuits (RFICs), mixed-signal integrated circuits, etc. For example, LNAs 240 and receive circuits 242 may be implemented on one module, which may be an RFIC, etc. The circuits in transceivers 220 and 222 may also be implemented in other manners.

In various embodiments, the data processor/controller 280 may perform various functions for the wireless device 110. For example, the data processor/controller 280 may process data received via receivers 230 and/or data transmitted via transmitters 250. The data processor/controller 280 may control the operation of the various circuits within the transceivers 220 and 222. A memory 282 may store program codes and data for data processor/controller 280. Data processor/controller 280 may be implemented on one or more application specific integrated circuits (ASICs) and/or other circuits.

In various embodiments, the wireless device 110 may support multiple frequency band groups, multiple radio technologies, and/or multiple antennas. The wireless device 110 may include one or more LNAs to support reception via the multiple frequency band groups, the multiple radio technologies, and/or the multiple antennas. In various embodiments, a printed circuit board (PCB) (or other substrate that supports circuitry) may support a coplanar waveguide, a surface launcher for a dielectric resonator antenna (e.g., a DRA that is part of the primary antenna array 210 or the secondary antenna array 212 of FIG. 2), and a metal structure to direct energy in many different directions. The PCB may have a dielectric substrate used as part of the DRA.

Figure 3:
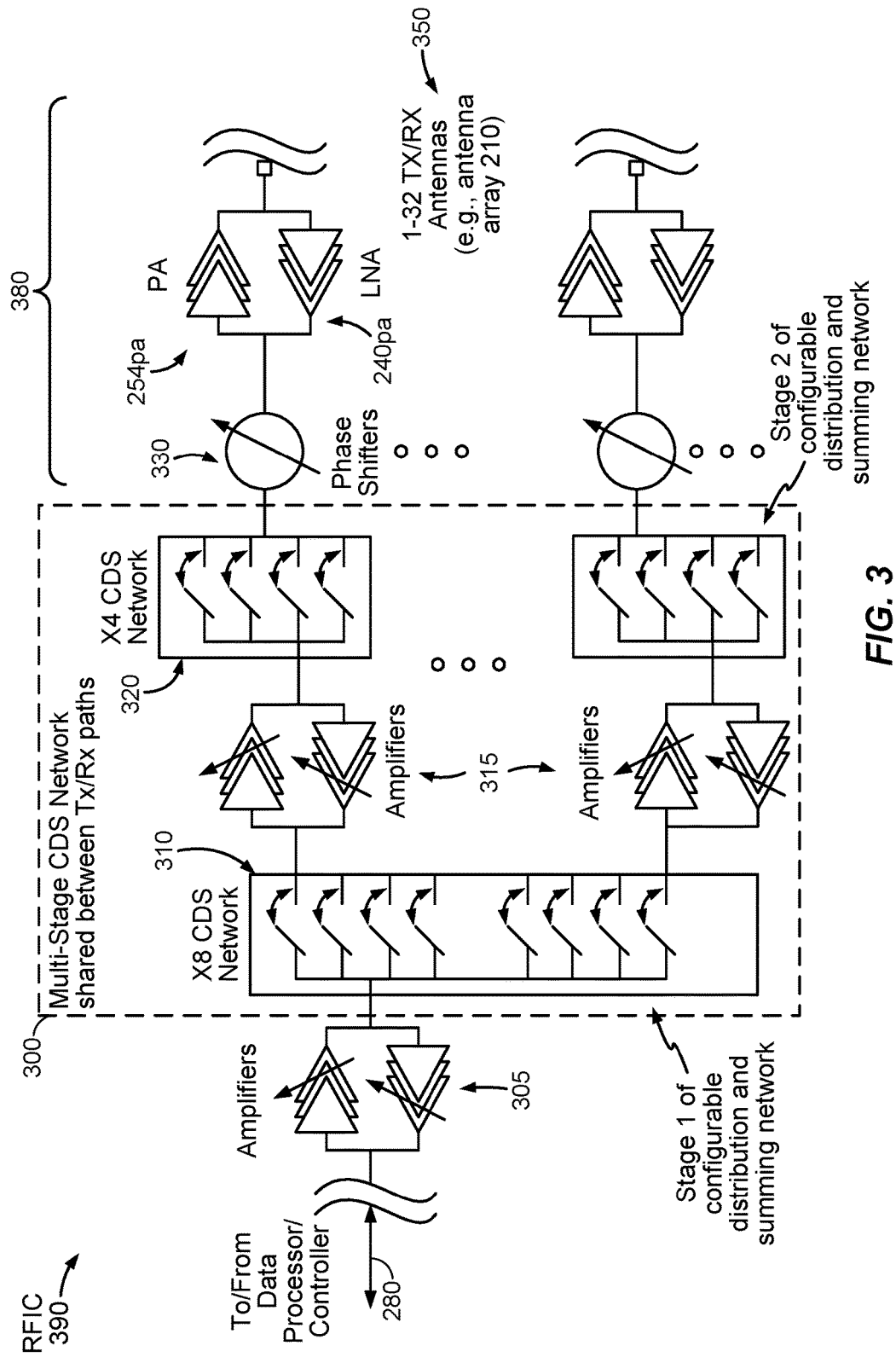
FIG. 3 illustrates an example architecture with multiple configurable distribution and summing networks, according to various aspects.

According to various aspects, FIG. 3 illustrates an example radio frequency integrated circuit 390 with an architecture that includes multiple configurable distribution and summing (CDS) networks. For example, in FIG. 3, the radio frequency integrated circuit 390 includes a first CDS network 310 and a second CDS network 320, which may each be associated with an antenna array (e.g., one of the antenna arrays 210, 212 shown in FIG. 2). An exemplary CDS system 300 may include multiple CDS networks, such as the CDS networks 310, 320. The first CDS network 310 may correspond to a first stage of the CDS system 300, and the second CDS network 320 may correspond to a second stage of the CDS system 300. A CDS network may be used with multiple antennas 350 (e.g., antennas of the antenna array 210 or 212). The CDS network may be used to maintain reasonable return loss and very low insertion loss over all configurations of a configurable antenna array.

During signal reception, signals from up to thirty-two antennas may be routed through the CDS network(s) and combined to form a combined signal. For example, the antenna(s) 350 may receive external signals (e.g., RF signals) and provide a received signal via an antenna interface circuit (e.g., the antenna interface circuit 224) to the LNA 240 pa. The LNA 240pa amplifies an input signal and provides an output signal to the CDS system 300 via phase shifters 330, as shown. The CDS system 300 includes multiple stages separated by amplifiers (e.g., amplifier circuits). For example, during signal reception, a stage of the CDS system 300 corresponding to the CDS network 320 may receive a signal from the phase shifters 330. The signal may travel through the CDS network 320, where each switch of the CDS network 320 is on or off depending on a selected antenna configuration. The CDS network 320 may output a signal that is amplified (e.g., by amplifiers 315) and provided to a "next" stage of the CDS system 300 (e.g., the CDS network 310). The CDS/amplifier process may be repeated as the signal travels through additional stages of a CDS system. An output of the CDS system 300 may be amplified by amplifiers 305 and provided to a data processor/controller (e.g., the data processor/controller 280), as shown. In an exemplary embodiment, the CDS system 300, the phase shifters 330, and the amplifiers 305 may correspond to (e.g., may be included within) the receive circuits 242 and/or the transmit circuits 252 of FIG. 2. In an exemplary embodiment, the stage(s) of the CDS system 300 (e.g., the CDS networks 310, 320), the amplifiers 305, the amplifiers 315, the phase shifters 330, the PA 254, and/or the LNA 240 are included in the RFIC circuit 390.

During signal transmission, the data processor/controller 280 provides a signal that is received by the CDS system 300 via the amplifiers 305. The signal may travel through stages of the CDS system 300 (e.g., from the CDS network 310 via the amplifiers 315 to the CDS network 320), and an output of the CDS system 300 may be provided via the phase shifters 330 to the PA 254pa. The PA 254pa amplifies the input signal and provides a transmit signal having a target output power level. The transmit signal is transmitted via the antenna(s) 350. A switch of a CDS network, such as the CDS network 320, may be opened when a corresponding path (e.g., of a plurality of paths 380) from the switch to an associated antenna 350 is not in use. The switch may be closed when the path from the switch to the associated antenna 350 is in use. In an illustrative embodiment, the switch may be opened and closed based on the value of a control signal. For example, the control signal may be received from the data processor/controller 280 or another device and may be provided to a gate of a transistor.

Those skilled in the art will appreciate that in alternative embodiments, the signal path(s) between antennas and a data processor/controller may include more, fewer, and/or different components than shown in FIG. 3. For example, in exemplary embodiments, a signal path may also include additional amplifiers, mixers, multipliers, an interface multiplexer (e.g., including high, medium, and/or low-pass filters), a wakeup detector, an RF controller, variable gain amplifiers, radio signal strength indicator (RSSI) measurement circuitry, etc.

Figure 4:
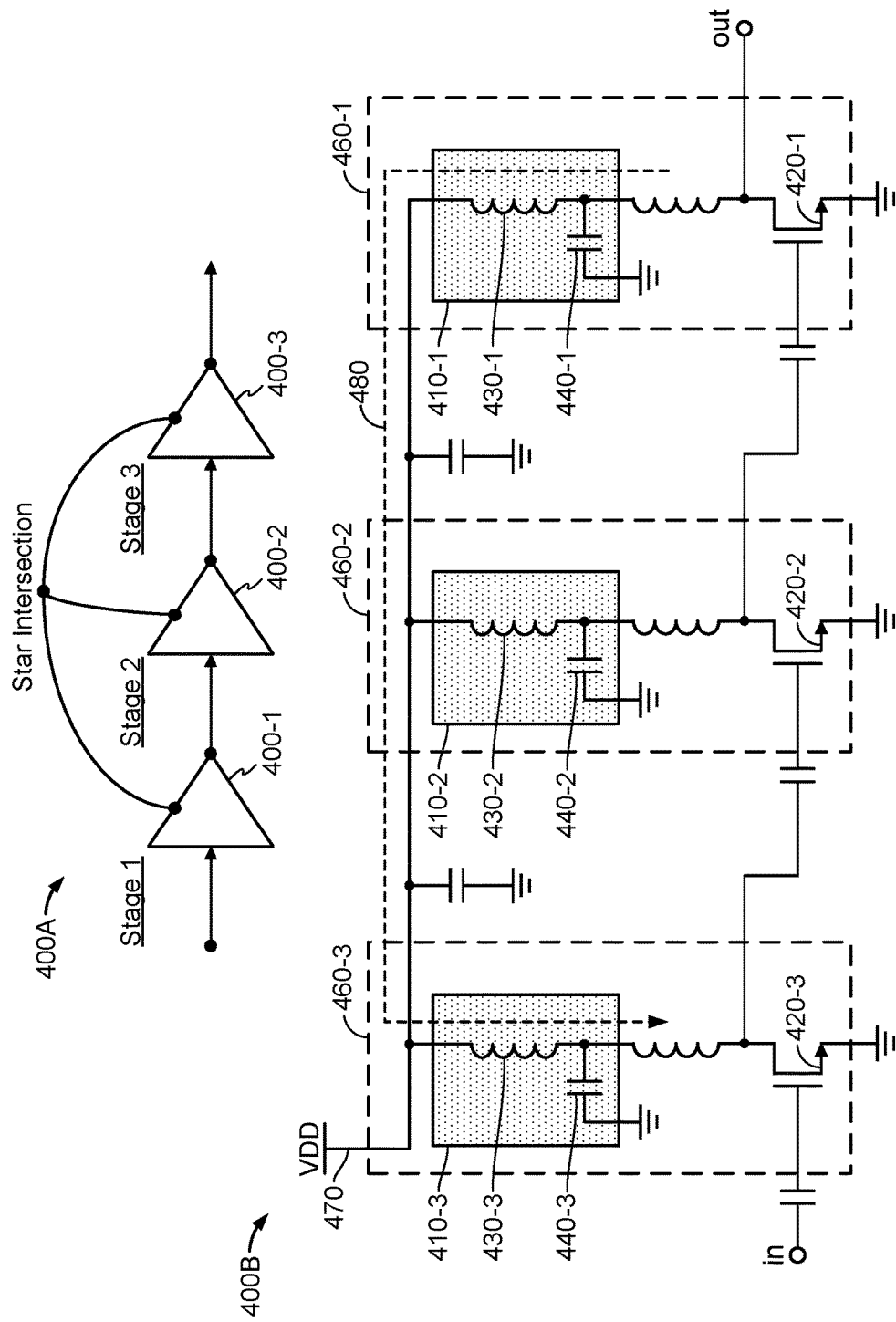
FIG. 4 illustrates example compact amplifier designs that are sensitive to instability, according to various aspects.

According to various aspects, FIG. 4 illustrates example compact amplifier designs that can be used in a millimeter-wave circuit (e.g., the amplifiers in the radio frequency integrated circuit 390 shown in FIG. 3). Generally speaking, compact amplifiers come with sensitivity to instability. For example, FIG. 4 illustrates an example compact amplifier 400A that may be sensitive to instability due to a supply network that couples output signals from successive gain stages 400-1, 400-2, 400-3 to inputs associated with the gain stages 400-1, 400-2, 400-3, shown in FIG. 4 as a star intersection. In devices where the gain stages 400-1, 400-2, 400-3 are in close proximity, the signals output from the gain stages 400-1, 400-2, 400-3 would couple onto the supply and thus lead to instability. The above-mentioned issues pertaining to the sensitivity to instability can be resolved via adding a passive filtering network on the supplies, thereby effectively isolating the supply pin(s) associated with each of the gain stages 400-1, 400-2, 400-3. For example, as shown at 400B, passive filtering networks 410-1, 410-2, 410-3 are introduced between a shared supply node 470 and a transistor 420-1, 420-2, 420-3 within each amplifier 460-1, 460-2, 460-3 to reduce the instability that may otherwise result from having the supply network couple output signals associated with the gain stages 400-1, 400-2, 400-3 to the inputs.

According to various aspects, as shown in FIG. 4, the passive filtering networks 410-1, 410-2, 410-3 each include a decoupling inductor structure 430-1, 430-2, 430-3 and an alternating current (ac) ground (bypass) capacitor 440-1, 440-2, 440-3 on the connections to the supplies to assure a complete current loop closure in the frame design. In various embodiments, each decoupling inductor structure 430-1, 430-2, 430-3 may be connected to the shared supply node 470 and the bypass capacitor 440-1, 440-2, 440-3 within the respective passive filtering network 410-1, 410-2, 410-3. Furthermore, each bypass capacitor 440-1, 440-2, 440-3 may be connected between ground the shared supply node 470 in a corresponding amplifier stage 460-1, 460-2, 460-3. Accordingly, the decoupling inductor structure 430-1, 430-2, 430-3 and the bypass capacitor structures 440-1, 440-2, 440-3 are used per amplifier stage 460-1, 460-2, 460-3 to isolate an undesired current 480 that may flow between any of the amplifier stages 410-1, 410-2, 410-3 and the shared supply node 470. The decoupling inductor structure 430-1, 430-2, 430-3 and the bypass capacitor structures 440-1, 440-2, 440-3 may thereby prevent the undesired current 480 from coupling back to the input(s) through the shared supply node 470. In particular, as shown in FIG. 4, each decoupling inductor structure 430-1, 430-2, 430-3 is connected in series between the shared supply node 470 and a signal path in the corresponding amplifier stage 460-1, 460-2, 460-3 and each bypass capacitor 440-1, 440-2, 440-3 is connected to ground, which creates a high impedance to isolate the undesired current 480 from coupling onto the inputs to each amplifier stage 460.

According to various aspects, FIG. 5 illustrates an example radio frequency integrated circuit 500 with a compact bypass capacitor and decoupling inductor structure that may address at least the above-mentioned issues in compact amplifier designs and other millimeter-wave circuits. More particularly, the radio frequency integrated circuit 500 shown in FIG. 5 may be used as the passive filtering networks 410-1, 410-2, 410-3 shown in FIG. 4, which may resolve issues pertaining to the significant area otherwise required to house decoupling and bypass structures per amplifier stage 460-1, 460-2, 460-3. In particular, the radio frequency integrated circuit 500 may combine a decoupling inductor 550 over a bypass capacitor 520, wherein the decoupling inductor 550 may comprise an 18 μm by 18 μm three-dimensional (3D) inductor structure in one example design. In various embodiments, the decoupling inductor 550 may be designed to have a self-resonance as close as possible to the frequency band at which a device incorporating the radio frequency integrated circuit 500 operates (e.g., 60 GHz when implemented in an 802.11ad WiGig transceiver configured to transmit and receive millimeter-wave wireless signals in a 60 GHz frequency band, 28 GHz and/or 39 GHz when implemented in a cellular transceiver configured to transmit and receive millimeter-wave wireless signals, etc.). As such, having the self-resonance associated with the decoupling inductor 550 close to the operating band may increase series isolation and introduce substrate losses that facilitate a damped supply network without the need to introduce resistance on the supply line, which will result with supply IR-drop.

For example, referring to the illustrative design shown in FIG. 5, the radio frequency integrated circuit 500 may include a grounded substrate 510 and a mid-metal ground plane 530 connected to a ground pin 505. The decoupling inductor 550 is disposed over the mid-metal ground plane 530 and connected to a supply pin 560 and a circuit pin 540 (e.g., to connect the radio frequency integrated circuit 500 to a supply and amplifier circuitry, as shown in FIG. 4). According to various aspects, the bypass capacitor 520 may be introduced below the mid-metal ground plane 530 and above the grounded substrate 510, wherein the bypass capacitor 520 may include a portion coupled between the mid-metal ground plane 530 and the grounded substrate 510 and one or more portions that are coupled to the circuit pin 540 and the decoupling inductor 550. In various embodiments, the bypass capacitor 520 may be formed from one or more active elements (e.g., transistors, accumulation mode capacitors, etc.).

Accordingly, the radio frequency integrated circuit 500 with the combined decoupling inductor 550 over the bypass capacitor 520 may substantially reduce the area associated with gain elements (e.g., in a power amplifier, low noise amplifier, variable gain amplifier, etc.) and improve instability concerns and/or risks in millimeter-wave circuits that may have amplifiers that are in close proximity and sensitive to instability. Furthermore, the design shown in FIG. 5 may provide damping in the supply network to prevent high-Q resonances, which generally refers to a ratio between energy loss relative to energy stored (e.g., a high-Q resonance may result in coupling at lower or higher frequencies, which can cause oscillations at these frequencies or ringing effects at the supplies). Further still, as shown in FIG. 6 through FIG. 15, the design associated with the radio frequency integrated circuit 500 may provide simpler matching between blocks.

Figure 6:
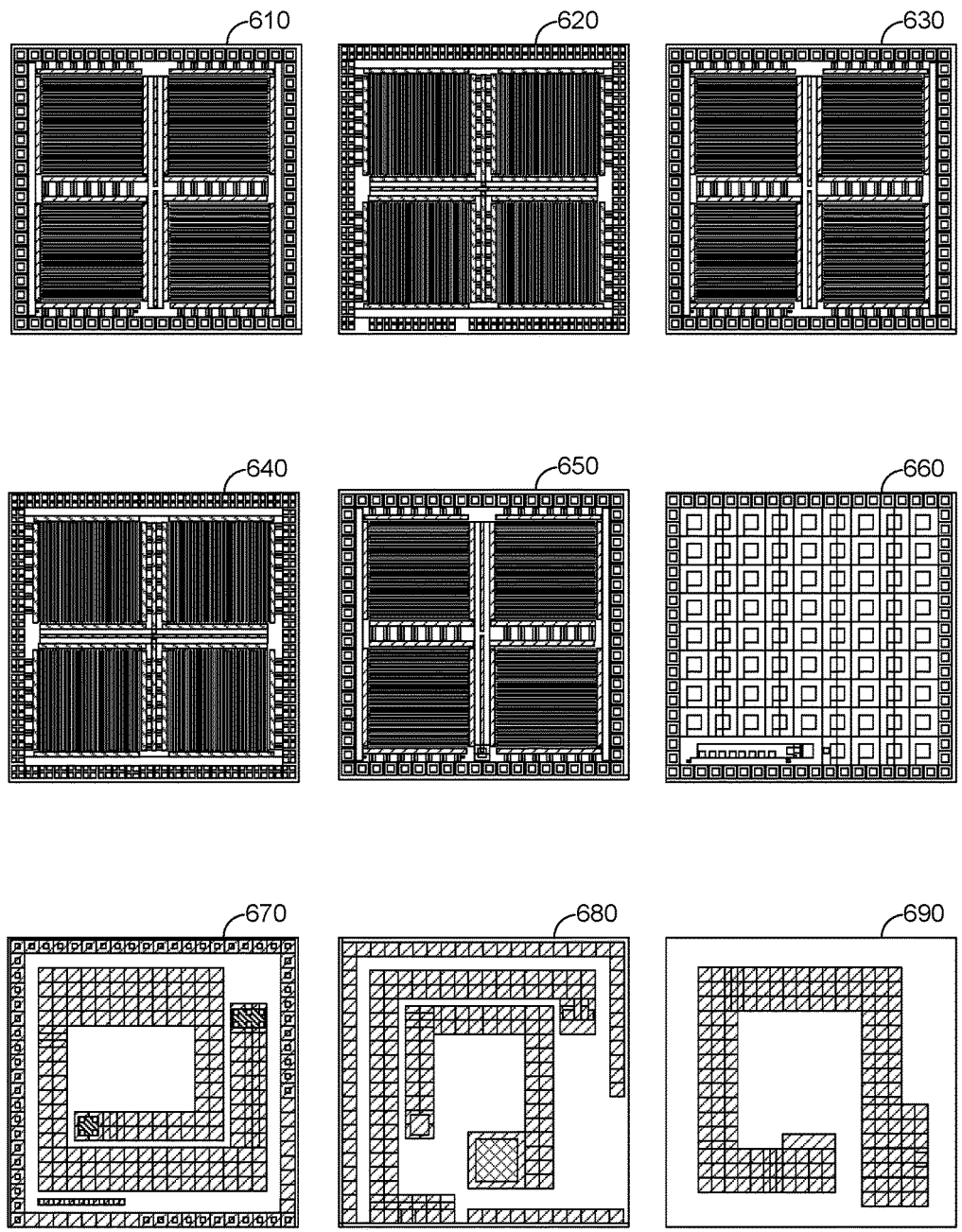
FIG. 6 through FIG. 15 illustrate an example layer-by-layer design in a specific radio frequency integrated circuit implementing the compact bypass capacitor and decoupling inductor structure shown in FIG. 5, according to various aspects.

More particularly, FIG. 6 through FIG. 15 generally illustrate an example layer-by-layer design in a specific radio frequency integrated circuit implementing the compact bypass capacitor and decoupling inductor structure shown in FIG. 5. In FIG. 6, the radio frequency integrated circuit includes various layers 610, 620, 630, 640, 650, 660, 670, 680, 690 that include one or more blocks that are matched to one another and connected through one or more interlayer vias. For example, the various layers 610, 620, 630, 640, 650, 660, 670, 680, 690 are shown together in FIG. 6 to illustrate the relationships among the circuit block designs, and FIG. 7 through FIG. 18 show the various individual layers and the connections to adjacent layers in more detail.

Figure 7:
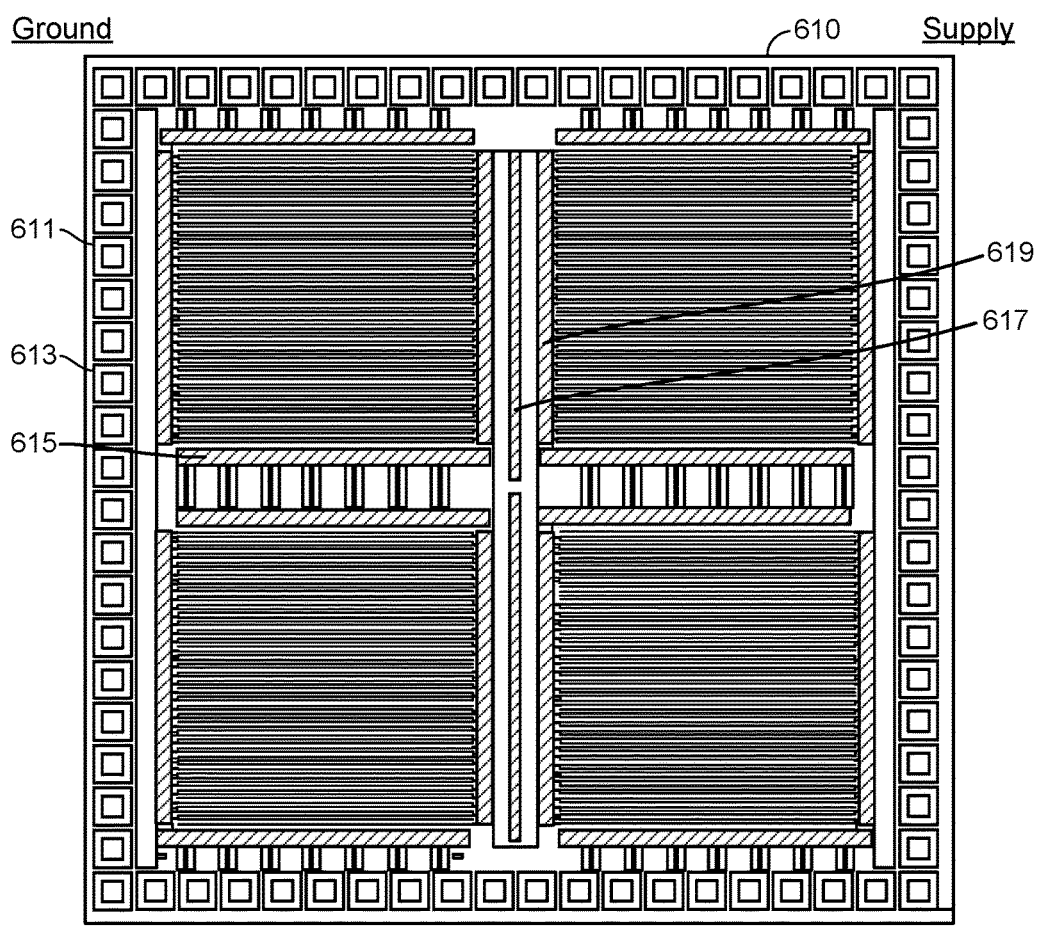
Figure 8:
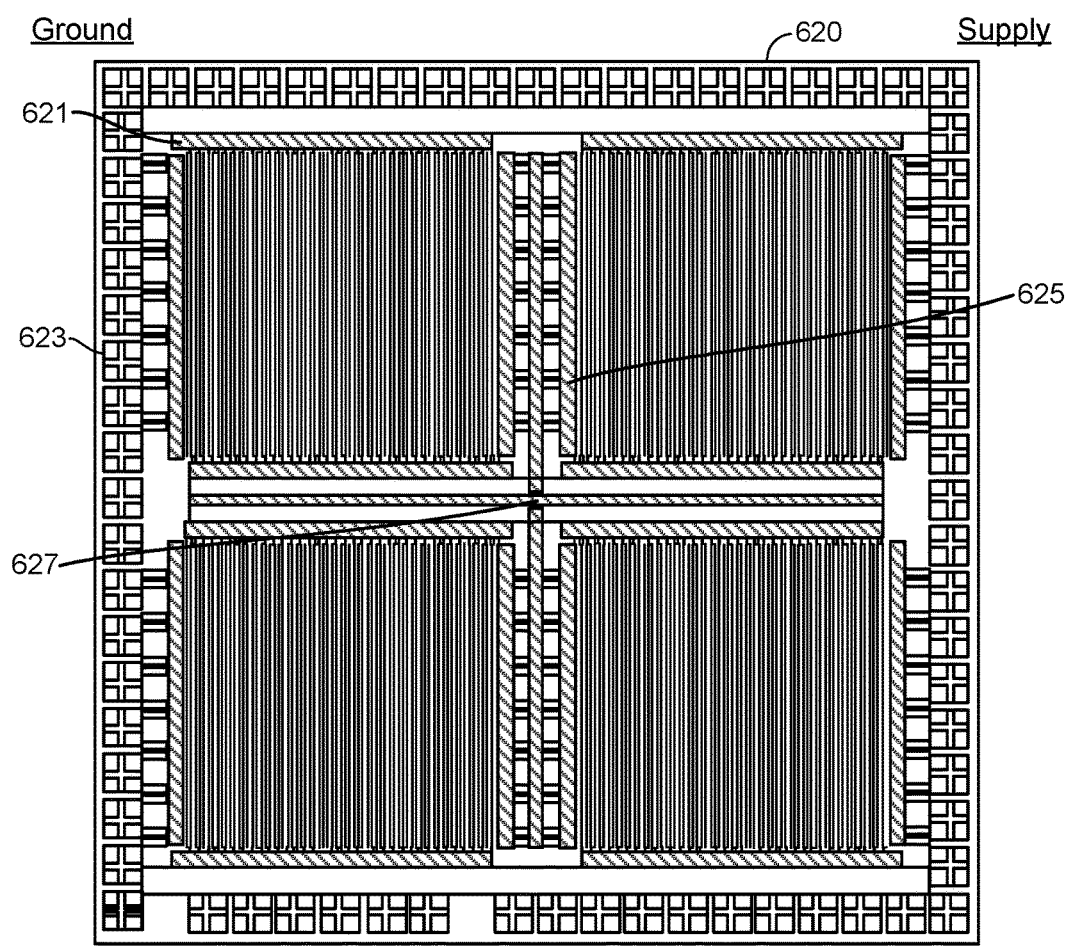

For example, referring to FIG. 7, a first layer (M1) 610 may be a bottom-most layer of the bypass capacitor. The first layer 610 has various substrate contacts and diffusion elements 611 that form a metal frame connected to ground. The first layer 610 further includes various electrical lines that are coupled to a supply node and to ground. Furthermore, the substrate contacts and diffusion elements 611 that form the metal frame around the perimeter of the first layer 610 are also connected to ground. In various embodiments, the first layer 610 may further include various vias 613, 615, 617, 619 that are located at poles of the bypass capacitor and provide points at which to connect the first layer 610 to a second layer (M2) 620, which is shown in FIG. 8.

Figure 9:
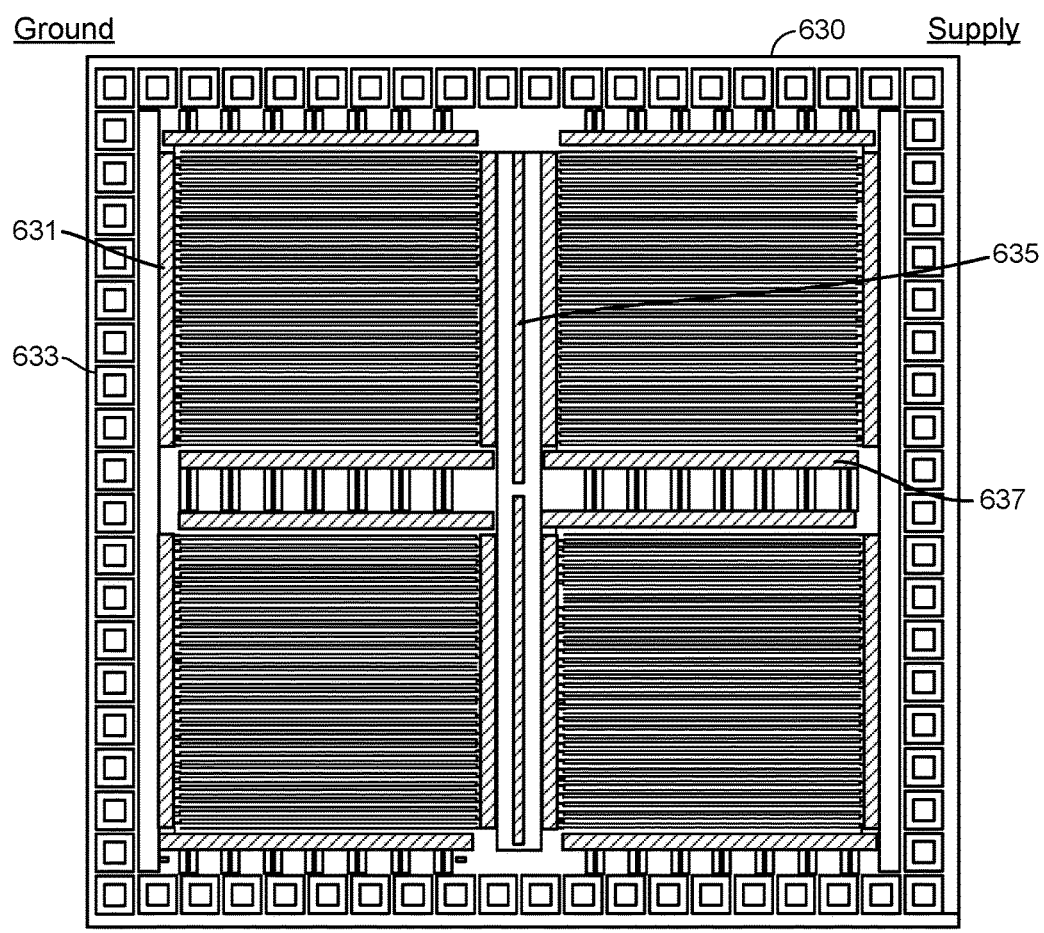
Figure 10:
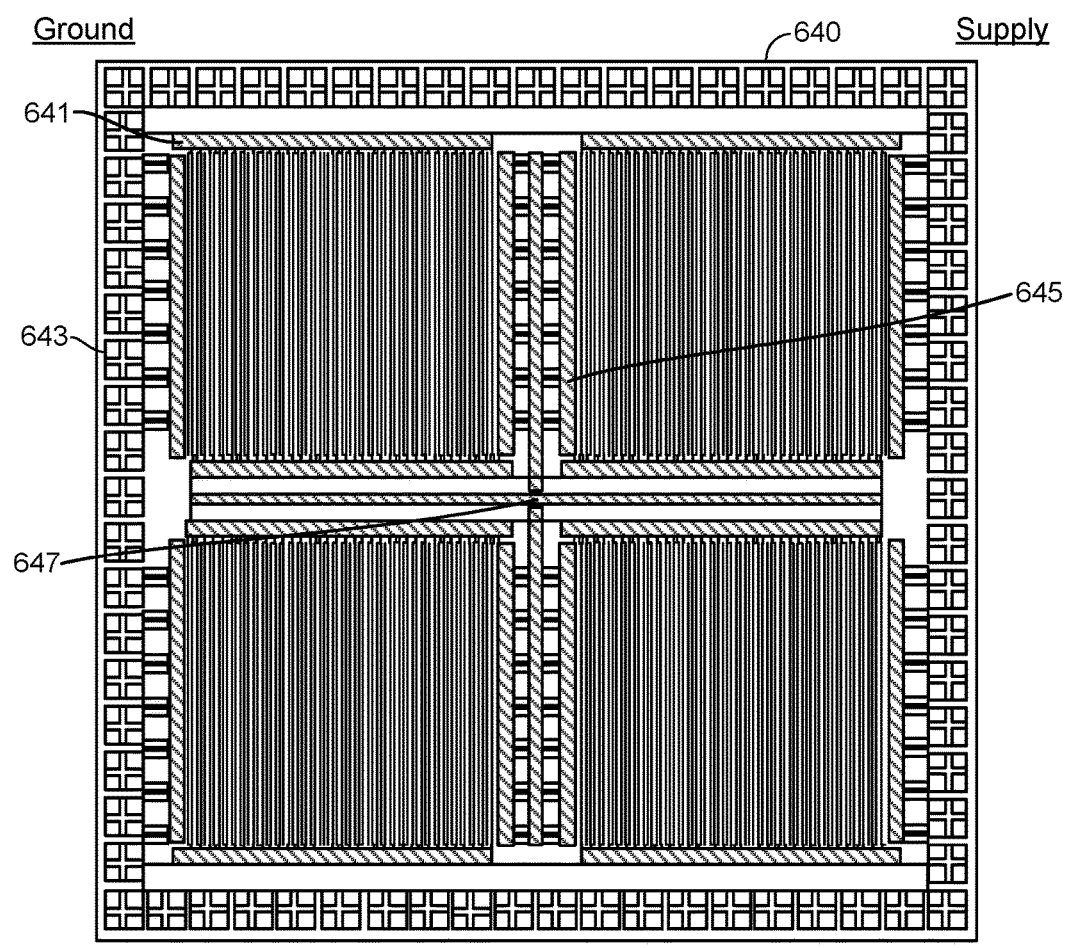
Figure 11:
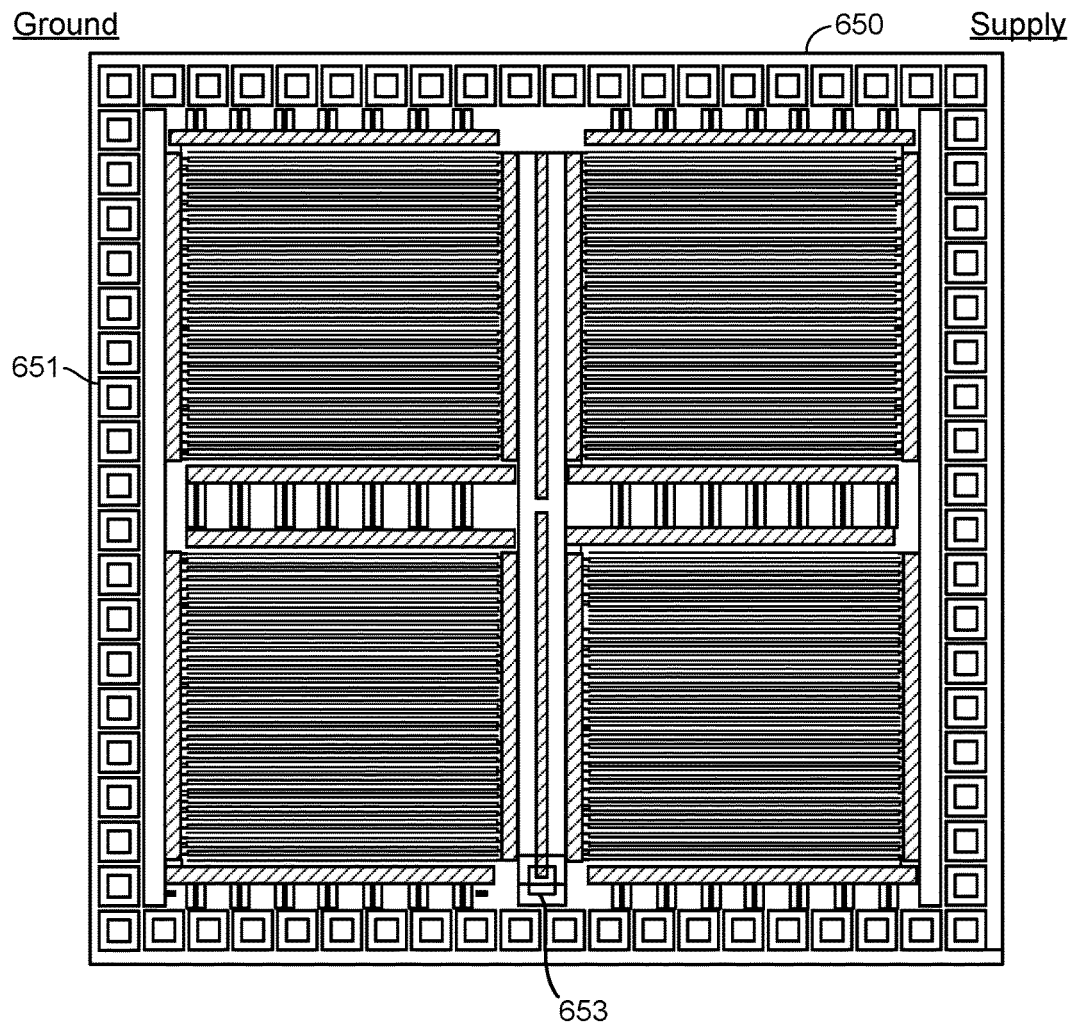

Accordingly, the vias 613, 615, 617, 619 may connect metal in the first layer 610 to metal in the second layer 620. In the second layer 620, the electrical lines that are configured to generate the capacitance may be arranged in a direction orthogonal to the electrical lines that are configured to generate the capacitance in the first layer 610. For example, in FIG. 7, the electrical lines that are configured to generate the capacitance in the first layer 610 are arranged in a horizontal direction between the supply node and ground, whereas the electrical lines that are configured to generate the capacitance in the second layer 620 as shown in FIG. 8 are arranged in a vertical direction. Furthermore, in various embodiments, the second layer 620 may include similarly include vias 621, 623, 625, 627 to connect metal in the second layer 620 to metal in a third layer (M3) 630, which is shown in FIG. 9 as including vias 631, 633, 635, 637 to a fourth layer (M4) 640, which is shown in FIG. 10. In various embodiments, the fourth layer 640 may likewise include vias 641, 643, 645, 647 to a fifth layer (M5) 650, which is shown in FIG. 11. The first through fifth layers 610-650 may therefore form the bypass capacitor with the decoupling inductor formed over the bypass capacitor.

Figure 12:
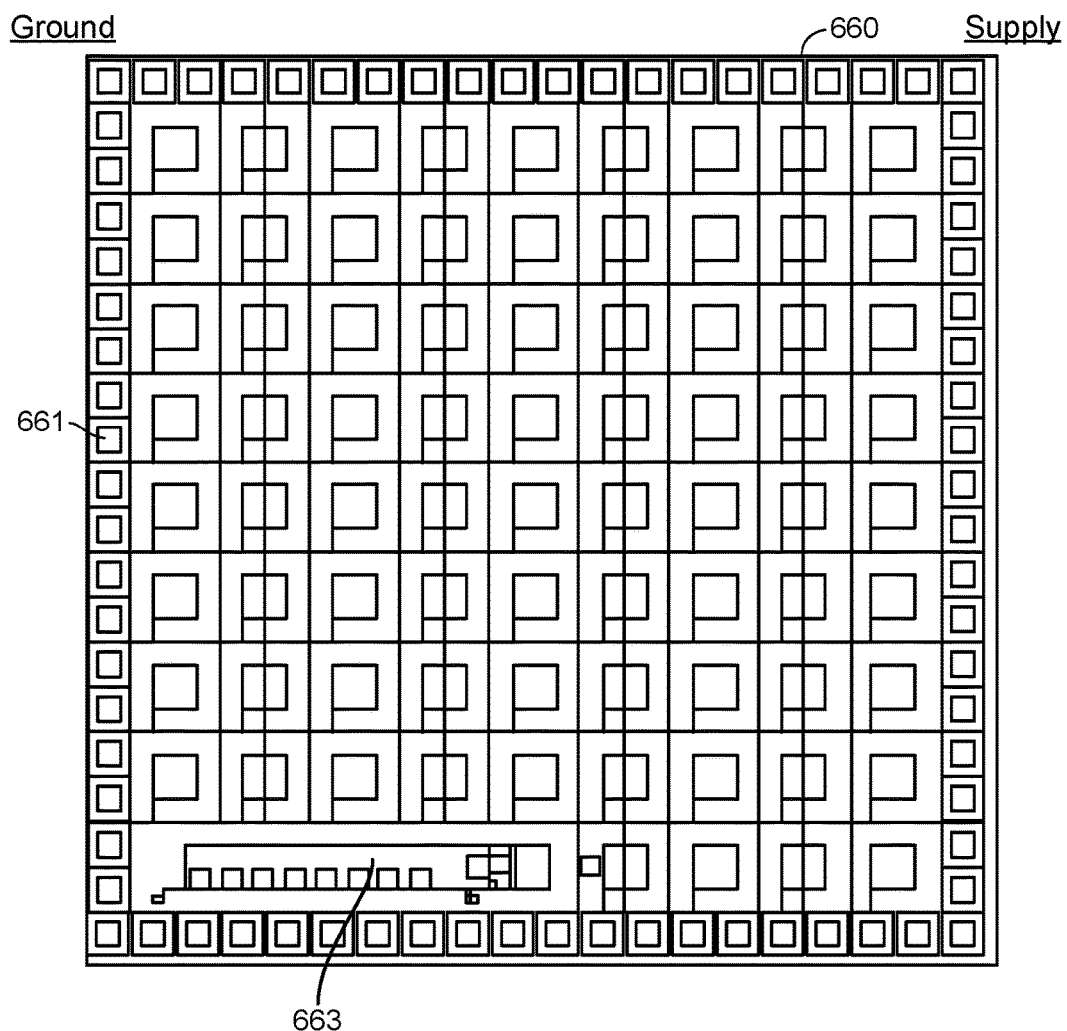
Figure 13:
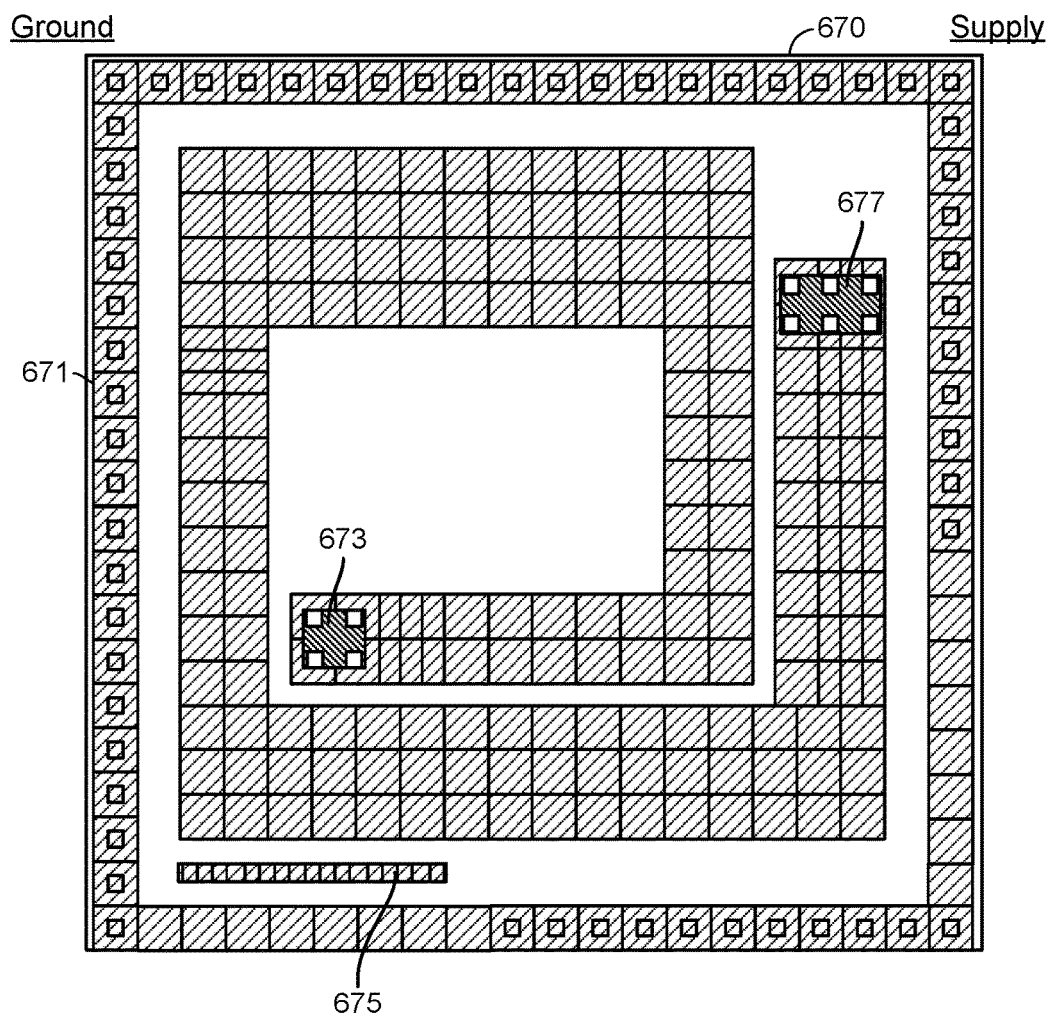
Figure 14:
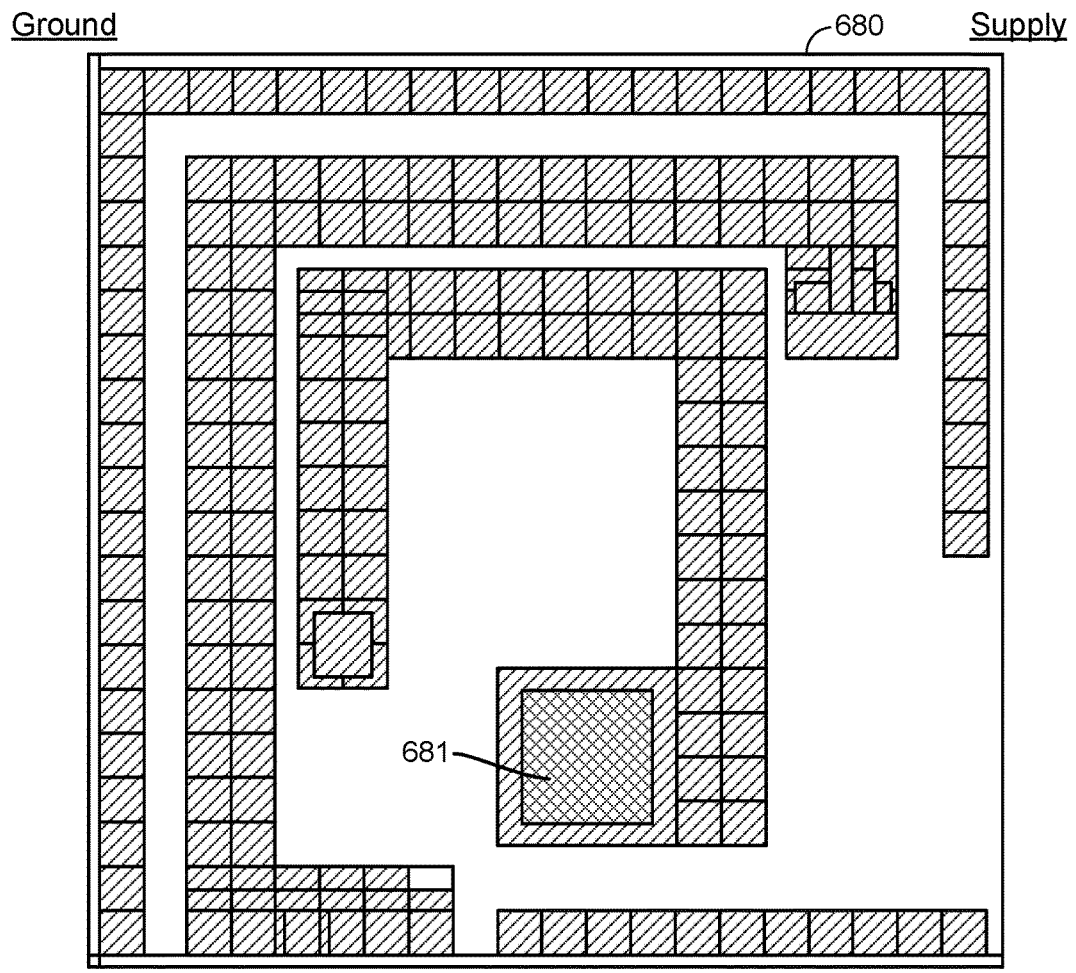
Figure 15:
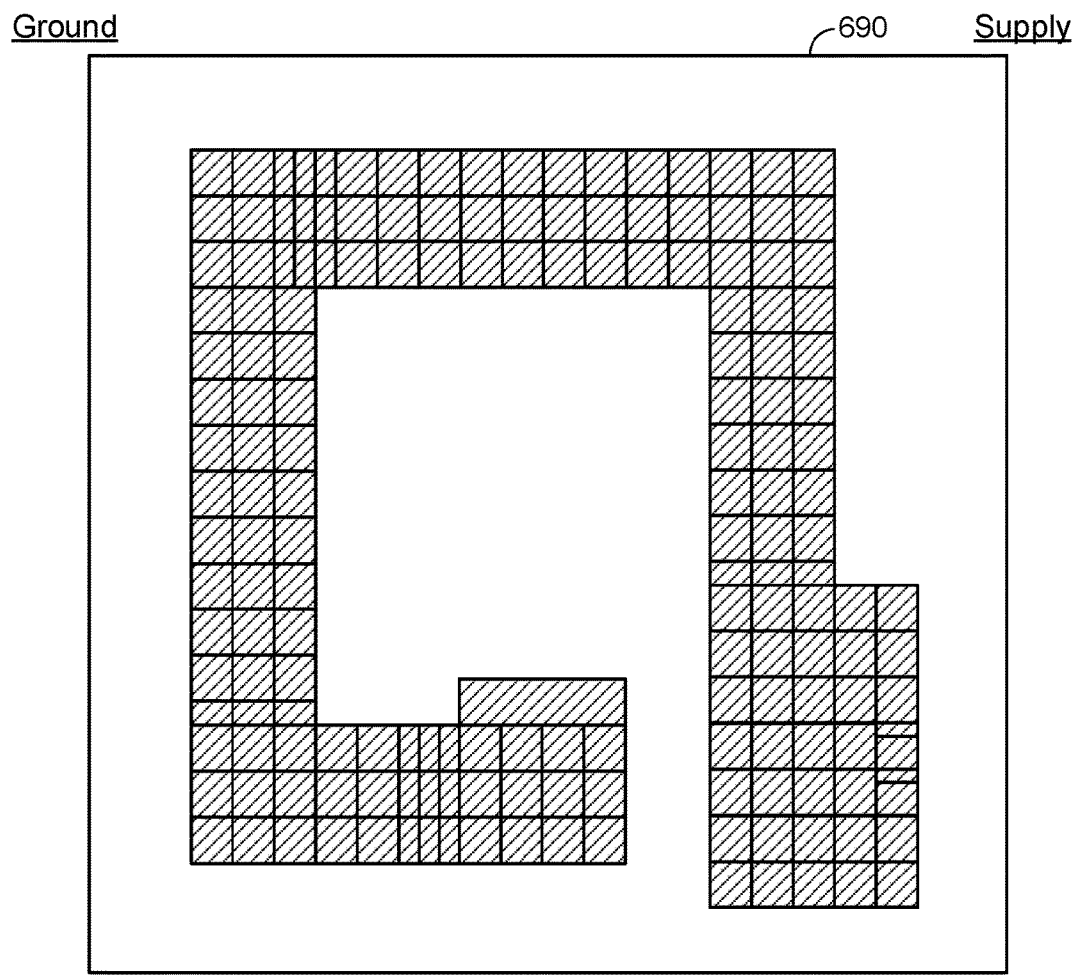

More particularly, referring to FIG. 11, the fifth layer 650 includes vias 651, 653 to connect to metal in a sixth layer (M6) 660, which is shown in FIG. 12. The sixth layer 660 may be a ground layer to provide isolation between the bypass capacitor and the decoupling inductor. As shown in FIG. 12, the ground layer 660 may include a via 663 through which the supply node can be connected to the cathode of the capacitor, thus providing the capacitor between the supply node and ground. According to various aspects, the ground layer 660 may include vias 661, 663 to connect to metal in a seventh layer (M7) 670, as shown in FIG. 13. The seventh layer 670 may further include vias 671, 673, 675, 677 to connect to an eighth layer (M8) 680, which is shown in FIG. 14. In general, the seventh layer 670 and the eighth layer 680 may correspond to the decoupling inductor structure, and the eighth layer 680 may in turn includes vias 681 to a ninth layer (M9) 690, which is shown in FIG. 15. In particular, the ninth layer 690 may comprise a redistribution layer (RDL) that makes one or more input/output pads associated with the integrated circuit available in other locations. For example, in various embodiments, the ninth (RDL) layer 690 may include one or more pads, contacts, wiring, and/or other suitable circuitry to enable bonding (e.g., to connect the supply pin 560 shown in FIG. 5 to ground, to connect the circuit pin 540 shown in FIG. 5 to another circuit, such as circuitry associated with a power amplifier, a low noise amplifier, a variable gain amplifier, etc.).

Those skilled in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those skilled in the art will appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted to depart from the scope of the various aspects and embodiments described herein.

The various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices (e.g., a combination of a DSP and a microprocessor, a plurality of microprocessors, one or more microprocessors in conjunction with a DSP core, or any other such configuration).

The methods, sequences, and/or algorithms described in connection with the aspects disclosed herein may be embodied directly in hardware, in a software module executed by a processor, or in a combination of the two. A software module may reside in RAM, flash memory, ROM, EPROM, EEPROM, registers, hard disk, a removable disk, a CD-ROM, or any other form of non-transitory computer-readable medium known in the art. An exemplary non-transitory computer-readable medium may be coupled to the processor such that the processor can read information from, and write information to, the non-transitory computer-readable medium. In the alternative, the non-transitory computer-readable medium may be integral to the processor. The processor and the non-transitory computer-readable medium may reside in an ASIC. The ASIC may reside in an IoT device. In the alternative, the processor and the non-transitory computer-readable medium may be discrete components in a user terminal.

In one or more exemplary aspects, the functions described herein may be implemented in hardware, software, firmware, or any combination thereof. If implemented in software, the functions may be stored on or transmitted over as one or more instructions or code on a non-transitory computer-readable medium. Computer-readable media may include storage media and/or communication media including any non-transitory medium that may facilitate transferring a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, DSL, or wireless technologies such as infrared, radio, and microwave, then the coaxial cable, fiber optic cable, twisted pair, DSL, or wireless technologies such as infrared, radio, and microwave are included in the definition of a medium. The term disk and disc, which may be used interchangeably herein, includes CD, laser disc, optical disc, DVD, floppy disk, and Blu-ray discs, which usually reproduce data magnetically and/or optically with lasers. Combinations of the above should also be included within the scope of computer-readable media.

While the foregoing disclosure shows illustrative aspects and embodiments, those skilled in the art will appreciate that various changes and modifications could be made herein without departing from the scope of the disclosure as defined by the appended claims. Furthermore, in accordance with the various illustrative aspects and embodiments described herein, those skilled in the art will appreciate that the functions, steps, and/or actions in any methods described above and/or recited in any method claims appended hereto need not be performed in any particular order. Further still, to the extent that any elements are described above or recited in the appended claims in a singular form, those skilled in the art will appreciate that singular form(s) contemplate the plural as well unless limitation to the singular form(s) is explicitly stated.

What is claimed is:

1. An integrated circuit, comprising:
   a shared supply node; and
   a plurality of gain stages, wherein the plurality of gain stages each comprise:
      gain stage circuitry disposed in a signal path;
      a decoupling inductor having a first terminal connected to the shared supply node and a second terminal connected to the gain stage circuitry; and
      a bypass capacitor having a first terminal connected to ground and a second terminal connected to the gain stage circuitry and to the second terminal of the decoupling inductor.

2. The integrated circuit recited in claim 1, wherein the decoupling inductor and the bypass capacitor form a passive filtering network configured to isolate the gain stage circuitry from a current flowing on a supply line coupling the plurality of gain stages to the shared supply node.

3. The integrated circuit recited in claim 2, wherein the isolated current flows from a last one of the plurality of gain stages.

4. The integrated circuit recited in claim 1, wherein the decoupling inductor has a self-resonance substantially close to an operating band associated with the integrated circuit to increase series isolation in the integrated circuit, to introduce substrate losses that facilitate damping in a supply network that couples the plurality of gain stages according to a star intersection, and to prevent high-Q resonances.

5. The integrated circuit recited in claim 1, wherein the bypass capacitor comprises one or more active elements, including at least one of a transistor or an accumulation mode capacitor.

6. The integrated circuit recited in claim 1, incorporated into a transceiver configured to transmit and receive millimeter-wave wireless signals.

7. The integrated circuit recited in claim 6, wherein the transceiver comprises an 802.11ad transceiver configured to transmit and receive the millimeter-wave wireless signals in a 60 GHz frequency band.

8. The integrated circuit recited in claim 6, wherein the transceiver comprises a cellular transceiver configured to transmit and receive the millimeter-wave wireless signals in one or more of a 28 GHz frequency band or a 39 GHz frequency band.

9. The integrated circuit recited in claim 1, incorporated into a wireless device configured to transmit and receive millimeter-wave wireless signals.

10. A method for stabilizing a supply network, comprising:
    providing a shared supply node;
    providing a signal path comprising a plurality of gain stages; and
    providing a passive filtering network in each of the plurality of gain stages, wherein the passive filtering network comprises an inductor having a first terminal connected to the shared supply node and a second terminal connected to circuitry disposed in the signal path and a capacitor having a first terminal connected to ground and a second terminal connected to the circuitry disposed in the signal path and to the second terminal of the inductor.

11. The method recited in claim 10, wherein the inductor and the capacitor are configured to isolate the circuitry disposed in the signal path from a current flowing on a supply line coupling the plurality of gain stages to the shared supply node.

12. The method recited in claim 11, wherein the isolated current flows from a last one of the plurality of gain stages.

13. The method recited in claim 10, wherein the inductor has a self-resonance substantially close to an operating band associated with the circuitry disposed in the signal path.

14. The method recited in claim 10, wherein the capacitor comprises one or more active elements, including at least one of a transistor or an accumulation mode capacitor.

15. The method recited in claim 10, wherein the shared supply node, the signal path, and the bypass and decoupling structure are provided in a transceiver configured to transmit and receive millimeter-wave wireless signals.

16. The method recited in claim 15, wherein the transceiver comprises an 802.11ad transceiver configured to transmit and receive the millimeter-wave wireless signals in a 60 GHz frequency band.

17. The method recited in claim 15, wherein the transceiver comprises a cellular transceiver configured to transmit and receive the millimeter-wave wireless signals in one or more of a 28 GHz frequency band or a 39 GHz frequency band.

18. The method recited in claim 10, wherein the shared supply node, the signal path, and the bypass and decoupling structure are provided in a wireless device configured to transmit and receive millimeter-wave wireless signals.

19. A passive filtering circuit, comprising:
 an inductor having a first terminal connected to a shared supply node and a second terminal connected to gain stage circuitry; and
 a capacitor having a first terminal connected to ground and a second terminal connected to the gain stage circuitry.

20. The passive filtering circuit recited in claim 19, wherein the second terminal of the capacitor is further connected to the second terminal of the inductor.

21. The passive filtering circuit recited in claim 19, wherein the inductor and the capacitor are configured to isolate the gain stage circuitry from a current flowing on a supply line coupling the inductor to the shared supply node.

22. The passive filtering circuit recited in claim 19, incorporated into a wireless device configured to transmit and receive millimeter-wave wireless signals in one or more of a 28 GHz frequency band, a 39 GHz frequency band, or a 60 GHz frequency band.

* * * * *